United States Patent [19]

Laerdal

[11] 4,062,357
[45] Dec. 13, 1977

[54] RESPIRATOR MASK

[76] Inventor: Asmund Sigurd Laerdal, Stavanger, Norway

[21] Appl. No.: 670,370

[22] Filed: Mar. 25, 1976

Related U.S. Application Data

[63] Continuation of Ser. No. 458,655, April 8, 1974, abandoned.

[51] Int. Cl.$^2$ .............................................. A61M 15/00
[52] U.S. Cl. ................................................ 128/146
[58] Field of Search ............... 128/146.7, 146.6, 146, 128/145.5–145.8, 185, 142.4, 188, 195, 205, 206, DIG. 26, 77; 24/115 K, 121 R, 129 D, 129 R

[56] References Cited

U.S. PATENT DOCUMENTS

| 2,540,567 | 2/1951 | Bennett | 128/146.7 |
| 2,995,131 | 8/1961 | Elam et al. | 128/146 |
| 3,013,556 | 12/1961 | Galleher, Jr. | 128/146.7 |
| 3,330,274 | 7/1976 | Bennett | 128/146.7 |

FOREIGN PATENT DOCUMENTS

| 552,798 | 2/1958 | Canada | 128/146 |
| 442,710 | 1/1968 | Switzerland. | |
| 599,050 | 3/1948 | United Kingdom | 24/129 D |

Primary Examiner—Dalton L. Truluck
Assistant Examiner—Henry J. Recla
Attorney, Agent, or Firm—Marn & Jangarathis

[57] ABSTRACT

This invention relates to a disposable respirator mask.

The present mask includes a hollow contact rim formed from a plastics blow-moulding which is filled with compressed air.

Further, the mask is also foldable for storage purposes.

9 Claims, 9 Drawing Figures

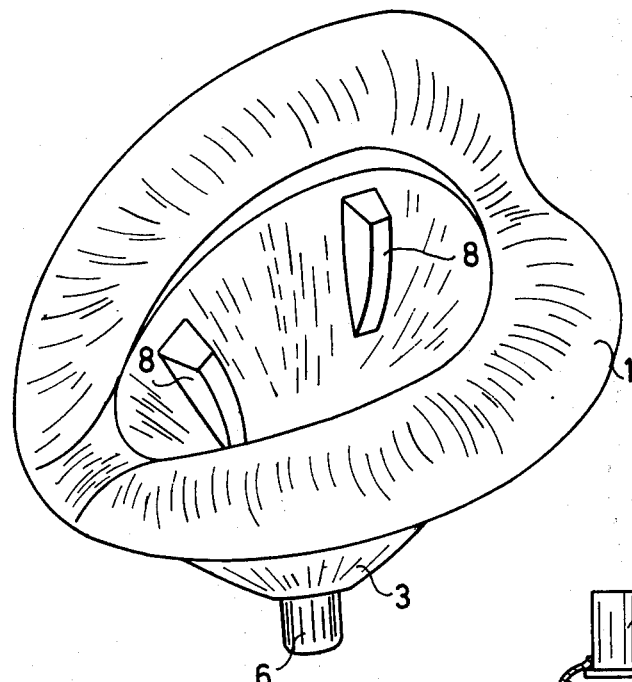
Fig. 4
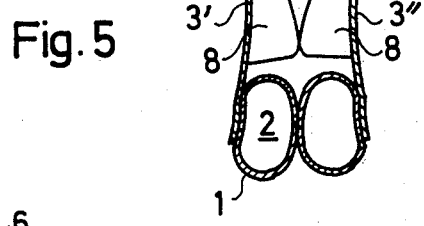
Fig. 5
Fig. 6
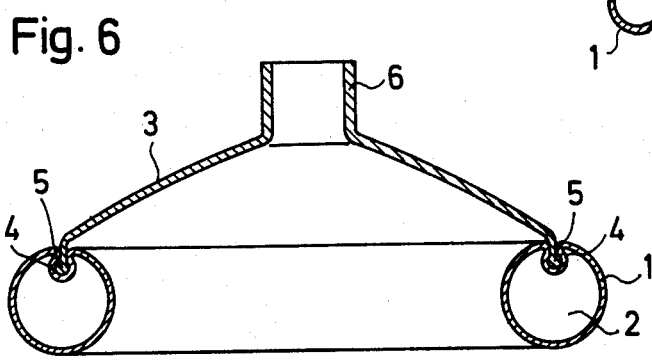

RESPIRATOR MASK

This is a continuation of application Ser. No. 458,655, filed Apr. 8, 1974 now abandoned.

This invention relates to a respirator mask and more especially to a disposable respirator mask.

Respirator masks for first aid and anaesthetic purposes having an inflatable contact rim, are known. Due to filling with air, the rim becomes resiliently elastic and can therefore adapt itself accurately to the face. In this way the desired close contact of the mask with the face is achieved.

The manufacture of the known inflatable rims for masks is relatively expensive. They are manufactured either by folding of a film of by the injection moulding process. Here special measures (gluing, welding) are necessary for the circumferential closure of the moulding, so that an interior space isolated from the outside is formed. A special closure device must be provided (compare, for example U.S. Pat. No. 3,695,264) so that the air remains in this interior space after inflating the the mask rim, and this also increases the total cost of the mask. Finally, a further disadvantage is that the mask is not always ready for use because the mask rim first has to be inflated and the closure device has to be actuated.

As far as respirator masks with a non-inflatable rim which is held in a taut or resiliently elastic state by a filling, for example, water (compare British Pat. Specification No. 840,638) have been disclosed, this rim also possesses the abovementioned disadvantages in technology of manufacture. Merely the closure device is eliminated.

Finally, non-inflatable rims for respirator masks have also already been manufactured by vulcanisation, which however is also relatively expensive.

The present invention is concerned with the task of providing a respirator with a contact rim which is resiliently elastic due to its filling and can be manufactured at substantially lower costs than the contact rims present in known respirator masks, and which also keeps the mask always ready for use. It is here intended that the manufacturing costs of the mask, even where they are caused by the mounting of the head-strapping, are so far lowered in total that it can be thrown away after a single use, which can be desired in many cases in order to avoid the danger of infection.

According to the present invention there is provided a respirator mask comprising a central portion and a hollow, plastics blow-moulded rim for contact with the face of a person, the interior of the rim being sealed from the atmosphere and being filled with a compressed gas.

Such a rim can be manufactured very cheaply by the blowing technique for the manufacture of hollow plastics bodies which is in itself known, above all if a moulding tool is employed here in which several rims can be manufactured in a single blowing step. Such a moulding tool, is for example, described in the Swiss Pat. Specification No. 442,710. For the manufacture of the mask rim plastics customary for processing by the blowing process, for example, polyethylenes and polyvinyl chlorides can be employed.

The present mask lowers the manufacturing costs for the mask to such an extent that the manufacture of respirator masks for single use appears economically justifiable. There is a demand for such masks in hospitals, above all for anaesthetic purposes. However, there is also the possibility of replacing only the contact rim in such (anaesthesia) masks, which requires an exchangeable fixture of the rim to the central part in general consisting of hard plastics. For this purpose formations, for example, in the shape of a groove, can be provided at the central part and at the rim, by means of which the two parts can be detachably joined to each other. After such a mask has been used, the contact rim is thrown away and the centre part is cleaned or disinfected.

The present mask can be constructed in such a way that it can be stored in a space-saving manner. However, care must be taken that normally it is not possible to exert such a pressure from outside on the permanently air-filled contact rim in the package (the internal pressure in the rim is slightly greater than the external pressure) that the rim bursts or that air is gradually forced out of the rim through the wall of the film which, to a certain, though only small extent, is permeable. In a preferred form the present mask provides that devices are shaped or moulded onto the centre part of the mask, which protect the air-filled contact rim, when the mask is folded up, against excessive compression.

In the case of a mask which can be folded up, the devices mentioned can consist of protrusions moulded onto the centre part of the mask on the sides of the wall parts facing each other after folding; these protrusions limit the distance between the wall parts. In this way, the aforementioned wall parts are prevented when folding up the mask, from an immediate mutual contact, which would subject the contact rim to an excessive pressure. The protrusions thus serve equally as spacers for the wall parts. Preferably the protrusions are shaped as strips which lie opposite each other and contact each other after folding.

For folding up the centre part of the mask, reduction zones are provided at the latter along the folding line or fold lines, as it is described in detail in the aforementioned United States patent specification. Herein, the wall parts of the centre part of the mask can be deflected away from the central blowing-in tube of the mask.

It is however, also possible to arrange the central air inlet tube of the mask at a centre part of the mask in such a way that it can be pressed in and that, after pressing in, it still protrudes a little, on both sides, beyond the contact rim, with its free end and with its end connected to the central part of the mask. By pressing in the blowing-in tube, the central part of the mask which, with the mask in working condition, domes considerably and therefore also requiring a relatively large space, obtains a space-saving flat form, the central part being placed inside the space surrounded by the air-filled contact rim. In the compressed state, the mask can therefore very easily be stored in First Aid Packs. In the compressed state of the mask, the blowing-in tube protrudes beyond the contact rim with both its ends and optionally also with the wall part of the central part of the mask immediately next to its end; this ensures that the rim cannot be subjected to excessive pressure when a pressure is exerted on the package from above or below. The pressure is absorbed by the aforementioned protruding parts and kept away from the contact rim. To make it possible to press in the central part of the mask or the air inlet tube, weakened zones are provided in shaping the central part of the mask by reducing the thickness of material at the central part of the mask around the tube.

In order to achieve a very simple and hence also cheap fixing of the ribbons or cording of the head-strapping to the mask, clamping members may be provided at the latter for pulling through and fixing the means of fastening, with infinite adjustability. For this purpose, the clamping members can possess two walls arranged at a distance from each other, between which the ribbons or cords can be pulled through and clamped tightly due to their inherent elasticity.

Illustrative embodiments of the invention will now be described with reference to the accompanying drawings, in which:

FIG 4 shows a perspective view of another embodiment of the mask;

FIG. 5 shows the mask of FIG. 4 in a folded condition, partially in section;

FIGS. 6 to 8 show sections through various embodiments of the present mask; and

Figure 7:
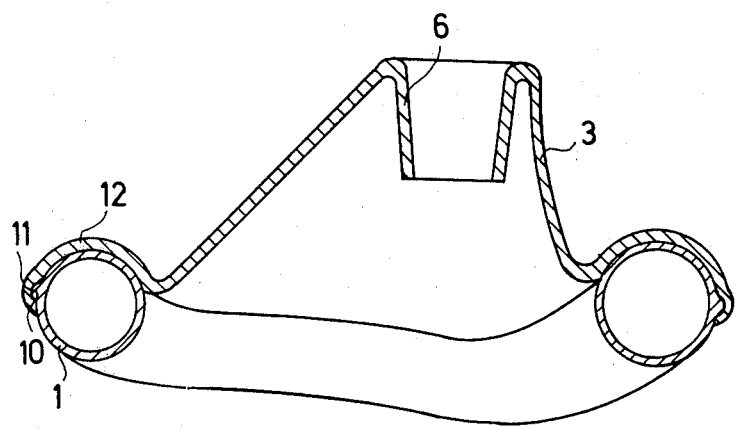
Figure 8:
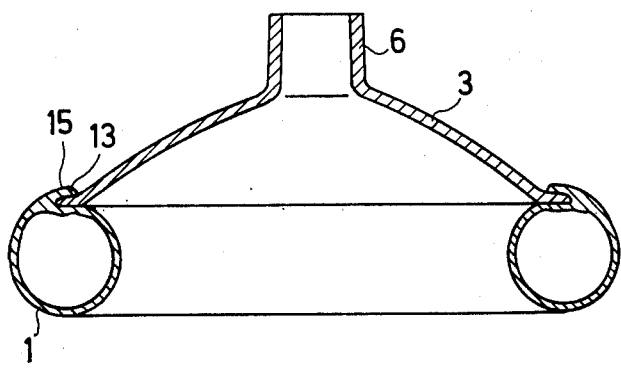

Referring to the drawings, there are shown masks which comprise a contact rim 1, constructed from a plastics blow-moulding having an interior space 2 which is filled with air and tightly and permanently isolated from the outside. The rim 1 can be firmly connected, for example, glued to the central part of the mask, designated as 3. It is however, also possible to fasten the rim to the central part of the mask in a detachable manner, as shown in FIGS. 6 to 8. For this purpose a groove 4 is moulded into the rim 1; the edge of the central part of the mask, is provided with a moulded rim 5 which can be firmly pressed into the groove 4, when the parts 1 and 3 are pressed against each other (FIG. 6). In the embodiment shown in FIG. 7, a rib 10 is moulded on the rim 1 for the same purpose; this rib can snap into a groove 11 formed at the edge of the central part 3. To receive the rim 1 in the edge of the central part 3 of the mask, the edge has a moulded recess 12 into which the rim 1 can be slid in and clamped, the interaction of the rib 10 and the groove 11 providing an additional securing of the strapping. In the embodiment shown in FIG. 8, a groove 13 is formed on the rim 1 by an extension 15, in which groove the edge of the central part 3 can be clamped tightly.

In the working condition, the central part 3 of the mask is relatively strongly domed; together with an inlet tube 6 which points centrally outwards from the central part of the mask, this results in a relatively large space requirement for storing the mask.

Figure 1:
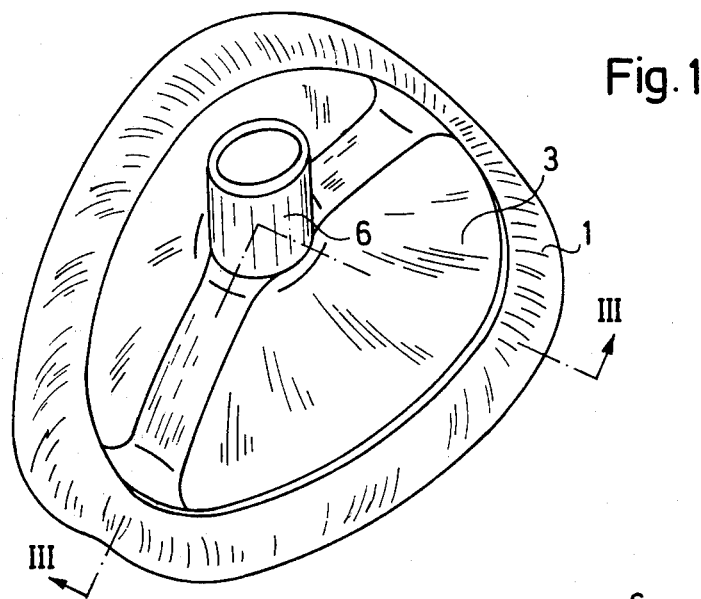
FIG. 1 shows a perspective view of one form of mask.
Figure 2:
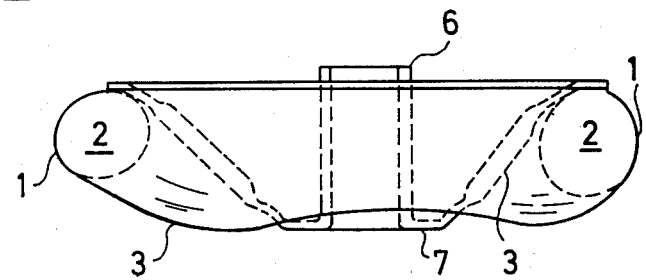
FIG. 2 shows the mask of FIG. 1 in a folded condition.
Figure 3:
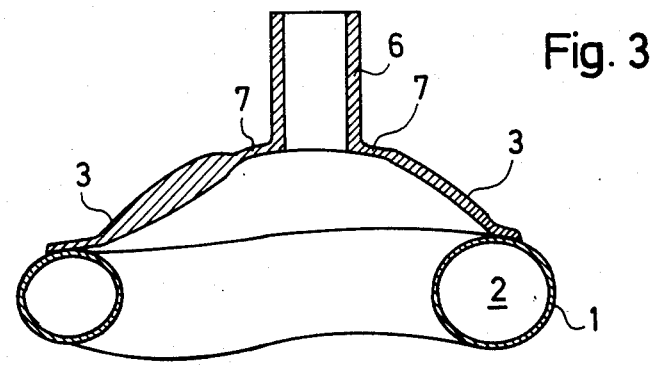
FIG. 3 shows a section taken along the line III—III of FIG. 1.

In order to reduce the space requirement substantially in the non-working condition of the mask, the embodiment shown in FIGS. 1 to 3 is provided with a tube 6 which can be pressed into the mask, with the central part of the mask turning inwards (compare FIG. 2). This is made possible by the thickness of the wall part 7 of the central part of the mask immediately adjacent to the tube 6 being substantially smaller than that of the remaining wall parts. By the reduction of wall thickness in the region of the wall part 7, a flexing zone is created here which makes it possible to press in the tube 6 and turn the central part 3 of the mask inwards in spite of the relatively hard construction of the latter.

As can be seen in FIG. 2, the tube 6 protrudes after it has been pressed into the mask, with both its ends above and below beyond the contact rim 1, whereby the latter is protected against too strong a compression if a pressure is exerted on the upper and/or lower side of the compressed mask. On one side (at the bottom in FIG. 2), the protruding wall part 7 also forms a counter bearing for a pressure acting on the mask. The correct measure of pressing in, for the bearing action of the two ends of the tube 6, can be achieved by the design of the extent of the reduction zone 7.

The mask shown in FIGS. 4 and 5 is provided with wall parts 3' and 3" of the central part of the mask, which lie on either side of the folding zone, being placed opposite each other (compare FIG. 5). Two weakness zones or flexing zones are provided for deflectability of the wall parts 3' and 3", in accordance with French Patent Specification No. 7,031,943. These zones, again created by reduction of the wall thickness of the central part 3 of the mask, extend over the central region of the central part of the mask along lines which extend across the largest dimension of the central part of the mask at a distance corresponding to the diameter of the tube 6. This is not represented in detail in the drawing. On the inside of the wall parts 3' and 3" of the central part of the mask, strips 8 are moulded, lying opposite each other, which come into contact on folding the mask. In this way, the possible distance between the wall parts 3' and 3" is limited and the contact rim 1 is protected from too large compressions (compare FIG. 5).

Figure 9:
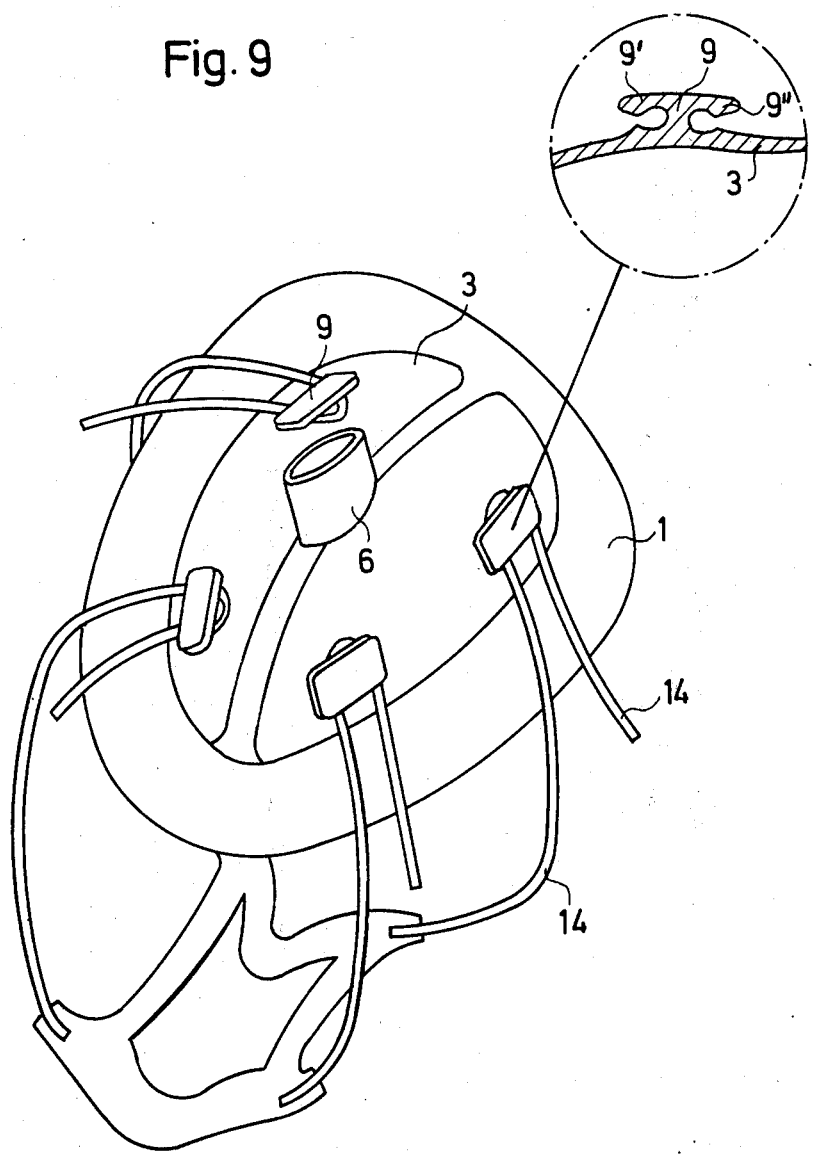
FIG. 9 shows a view of a mask at which clamping parts for the pulling through and the fixing, with infinite adjustability, of the cords of the head-strapping are provided.

In the mask shown in FIG. 9, a T-shaped clamping part 9, preferably of plastics, is provided at the central part 3 on its outer side, that is to say the side away from the face moulded on, for example, at the central part 3 (compare the partial enlargement). The cords 14 of the head-strapping can be pulled through between the flaps 9' and 9" and the wall of the central part 3 of the mask and clamped in tightly in any position. As a result, an infinitely variable adjustment of the cords 14 and hence an entirely individual adaptation of the head-strapping to the individual conditions of each case is possible. The T-shaped form proves suitable for the reason that the ends of the cords 14 can thereby be reflected and fixed so that they do not cause interference in front of the central part of the mask. Of course, the clamping parts can also take another form, for example, they can be made U-shaped. In any case, the clamping action arises from the inherent elasticity of the flaps of the clamping parts.

I claim:

1. A respirator mask which comprises: a yieldably resilient deformable circumferential rim formed of a plastics material for contacting the face of a person; and a central portion peripherally attached to said rim and including an air inlet tube, said central portion having a single-walled structure made from a deformable plastics material and being dome-shaped and including at least one substantially annular area of locally reduced thickness surrounding the air inlet tube adjacent thereto having sufficient flexibility for facilitating bulging in of the central portion the interior area bound by into said rim whereby the central portion is maintained in said area.

2. The respirator mask as defined in claim 1 and including clamping member means disposed on said central portion for receiving clamping cords for securing said mask to the head of a person, each clamping member means defining a channel between two walls for receiving and elastically clamping said cords.

3. The respirator mask as defined in claim 2 wherein the exterior portion of said mask is provided with T-shaped members with elastically deformable flaps clamping cords associated with said clamping member for securing said mask to the head of a person.

4. The respirator mask as defined in claim 1 wherein said central portion is provided with a terminal rib means for detachable mounting of said hollow rim.

5. The respirator mask as defined by claim 4 wherein said rim is formed with groove means and said central portion is formed with terminal rib means which detailably engage said groove means of said rim.

6. A respirator mask according to claim 1 wherein said central portion additionally includes an annular area of reduced thickness about the periphery of the central portion and adjacent the deformable rim.

7. A respirator mask according to claim 1 wherein said deformable rim is hollow, is filled with a gas and is permanently sealed from the atmosphere.

8. A respirator mask according to claim 7 wherein said air inlet tube extends beyond said rim in the bulged-in state.

9. The respirator mask as defined in claim 7 wherein said hollow rim is blow molded.

UNITED STATES PATENT OFFICE
CERTIFICATE OF CORRECTION

Patent No. 4,062,357            Dated December 13, 1977

Inventor(s) Asmund Sigurd Laerdal

It is certified that error appears in the above-identified patent and that said Letters Patent are hereby corrected as shown below:

Column 4, line 64, after "by" delete "into" and insert -- into -- after "portion".

*Signed and Sealed this*

*Tenth* Day of *April 1979*

[SEAL]

Attest:

RUTH C. MASON  
*Attesting Officer*

DONALD W. BANNER  
*Commissioner of Patents and Trademarks*